(12) United States Patent
Ketelson

(10) Patent No.: US 7,276,552 B2
(45) Date of Patent: Oct. 2, 2007

(54) COMPOSITIONS AND METHODS FOR INHIBITING PROTEIN ON SURFACES

(75) Inventor: Howard Allen Ketelson, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 11/273,778

(22) Filed: Nov. 15, 2005

(65) Prior Publication Data

US 2006/0063904 A1    Mar. 23, 2006

Related U.S. Application Data

(63) Continuation of application No. 10/732,934, filed on Dec. 11, 2003, now abandoned.

(60) Provisional application No. 60/436,159, filed on Dec. 23, 2002.

(51) Int. Cl.
*C08F 20/56* (2006.01)
*C08F 32/26* (2006.01)

(52) U.S. Cl. .................. 524/555; 526/303.1; 510/112; 510/113; 514/839

(58) Field of Classification Search ................ 524/555; 526/303.1; 510/112, 113; 514/839
See application file for complete search history.

(56) References Cited

U.S. PATENT DOCUMENTS

| | | |
|---|---|---|
| 4,411,932 A | 10/1983 | Kwan |
| 5,720,976 A | 2/1998 | Kim et al. |
| 5,998,588 A | 12/1999 | Hoffman et al. |
| 6,096,138 A | 8/2000 | Heller et al. |
| 6,153,568 A | 11/2000 | McCanna et al. |
| 6,270,903 B1 | 8/2001 | Feng et al. |
| 6,274,133 B1 | 8/2001 | Hu et al. |
| 6,323,165 B1 | 11/2001 | Heller et al. |
| 6,426,086 B1 | 7/2002 | Papahadjopoulos et al. |
| 6,447,897 B1 | 9/2002 | Liang et al. |
| 6,486,213 B1 | 11/2002 | Chen et al. |
| 6,494,861 B1 | 12/2002 | Tsukernik |
| 6,582,926 B1 | 6/2003 | Chilkoti |
| 6,664,294 B1 | 12/2003 | Park et al. |
| 2002/0004466 A1 | 1/2002 | Xia et al. |
| 2002/0155241 A1 | 10/2002 | Tarasevich et al. |
| 2003/0175410 A1 | 9/2003 | Campbell et al. |

FOREIGN PATENT DOCUMENTS

| | | |
|---|---|---|
| JP | 6122779 | 5/1994 |
| JP | 2002 256075 | 9/2002 |
| WO | WO 02/30571 | 4/2002 |

OTHER PUBLICATIONS

Lee, et al., "Protein-Resistant Surfaces Prpeared by PEO-Containing Block Copolymer Surfactants", *Journal of Biomedical Materials Research*, vol. 23, 1989, pp. 351-368.
Huber, et al., "Programmed Adsorption and Release of Proteins in a Microfluidic Device", *Science*, vol. 301, Jul. 18, 2003; pp. 352-354.
Hsiue, et al., "Preparation of Controlled Release Ophthalmic Drops, for Glaucoma Therapy Using Thermosensitive Poly-N-Isopropylacrylamide" *Biomaterials*, vol. 23, 2002, pp. 457-462.
Kidoaki, et al., "Thermoresponsive Structural Change of a Poly(N-isopropylacrylamide) Graft Layer Measured with an Atomic Force Microscope", *Langmuir*, 2001, pp. 2402-2407.
Rochev, et al., "Surface Modification for Controlled Cell Growth on Copolymers of N-isopropylacrylamide", *Polymer Science*, vol. 118, 2001, pp. 153-156.
Chen, et al., Graft Copolymers Having Hydrophobic Backbone and Hydrophilic Branches, XVI Polystyrene Microspheres with Poly(N-isopropylacrylamide), *Polymres for Advanced Technologies*, vol. 10, 1999, pp. 120-126.
Ho, Interactions of PEO-Containing Polymeric Surfactants with Hydrophobic Surfaces, Chapter 2, "Solution Properties of Polyethylene Oxide in Water", *University of Utah*, 1988, pp. 14-46.
Bohanon, et al., Neural Cell Patern Formation on Glass and Oxidized Silicon Surfaces With Poly (N-isopropylacrylamide), vol. 8, No. 1, 1996, pp. 19-39.
Heskins, et al., Solution Properties of Poly (N-isopropylacrylamide), *Journal, Macrolol. Sci.-Chem.*, vol. A2(8), Dec. 1986, pp. 1441-1455.
Yamada, et al., "Membrane Properties of Polyethylene Films Photografted with Hydrophilic Monomers", *Polymer Gels and Networks*, vol. 2, 1994, pp. 323-331.
Dong, et al., "Chapter 16—Thermally Reversible Hydrogels", *American Chemical Society Symposium*, 1987, pp. 236-244.
Singer, Press Release, "Sandia Microfluidic Device Rapidly Captures and Releases Proteins, Science Reports", *Sandia National Laboratories, A Department of Energy National Laboratory*, Jul. 22, 2003, pp. 1-2.
Gutowska, et al., "Heparin Release From Thermosensitive Polymer Coatings: In Vivo Studies", *Journal of Biomedical Materials Research*, vol. 29, pp. 811-821 (1996).
Uchida, et al., Temperature-Dependent Modulation of Blood Platelet Movement and Morphology on Poly(N-isoproppylacrylamide)-Grafted Surfaces, *Biomaterials*, vol. 21, pp. 923-929 (2000).
Pichot, et al., "Hydrophilic Stimuli-responsive Particles for Biomedical Applications", *Macromol. Symposium*, vol. 175, pp. 285-297 (2001).

*Primary Examiner*—Helen L Pezzuto
(74) *Attorney, Agent, or Firm*—Julie Anne Knight; Gregg C. Brown

(57) ABSTRACT

The use of NIPAM polymers to prevent or reduce the formation of protein deposits on the surfaces of medical devices is described. The invention is particularly directed to reduction of the adsorption of proteins on surfaces of contact lenses and other medical prosthetics.

3 Claims, 1 Drawing Sheet

COMPOSITIONS AND METHODS FOR INHIBITING PROTEIN ON SURFACES

CLAIM OF PRIORITY

The present application is a continuation of patent application Ser. No. 10/732,934 filed Dec. 11, 2003, now abandoned which claims priority under 35 USC §119(e) from Provisional Application Ser. No. 60/436,159 filed Dec. 23, 2002.

BACKGROUND OF INVENTION

The present invention is directed to the reduction of protein deposition on surfaces. The invention provides compositions and methods for inhibiting the deposition of protein on the surfaces of medical devices, particularly biomedical and prosthetic devices. The invention is based on the discovery that certain polymers and related copolymers comprising the monomer n-isopropylacrylamide (NIPAM) significantly inhibit protein deposition on the surfaces of contact lenses.

Proteins adsorb to almost all surfaces and the minimization or elimination of protein adsorption has been the subject of numerous studies, such as those reported by Lee, et al., in *J. Biomed. Materials Res.*, vol. 23, pages 351-368 (1989). Sensors, chromatographic supports, immunoassays, membranes for separation, biomedical implants, prosthetic devices (e.g., contact lenses) and many other devices or objects can be adversely affected by protein adsorption. A method and/or means for treating the surfaces of such objects so as to prevent or reduce protein deposition would therefore be quite advantageous.

The use of NIPAM-containing polymers to modify surfaces and control protein deposition on glass and silicon substrates has been previously described. The following publications provide further background regarding such modifications:

1. Kidoki, et al., *Langmuir*, 17, pp. 2402-2407 (2001);
2. Bohanon, et al., *J. Biomater. Sci. Polymer Edn.*, Vol. 8, No. 1, pp. 19-39 (1996);
3. International (PCT) Patent Publication No. WO 02/30571 A2 (Sudor);
4. U.S. Pat. No. 6,447,897 (Liang, et al.);
5. U.S. Pat. No. 6,270,903 (Feng, et al.); and 6. Huber, et al., *Science*, Vol. 301, pp. 352-354, Jul. 18, 2003.

The above-identified publications do not disclose or suggest that NIPAM-containing polymers could be used to modify the surfaces of medical devices, such as contact lenses, and to control protein deposition and release on such surfaces.

The terms "soft" and "hard" relative to contact lenses are generally associated with not only the relative hardness of the respective types of lenses, but also the type of polymeric material from which the lenses are formed. The term "soft" generally denotes a contact lens that is formed from a hydrophilic polymeric material, such as hydroxyethyl methacrylate or "HEMA", while the term "hard" generally denotes a lens that is formed from a hydrophobic polymeric material, such as polymethylmethacrylate or "PMMA". The surface chemistry and porosity of the hard and soft lenses is quite different. Soft lenses typically contain a large amount of water, are quite porous, and bear ionic charges on the exposed surfaces of the lenses, while hard lenses are considerably less porous and generally do not bear ionic surface charges.

The ionic surfaces and porous nature of soft contact lenses can lead to significant problems when the lenses come into contact with the tear film due to the complex composition of the tear film, which is largely comprised of proteins, lipids, enzymes and various electrolytes. Tear components include albumin, lactoferrin, lysozyme and a number of immunoglobulins. The uptake of proteins from the tear fluid onto the lens is a common problem and depends on a number of factors, including the nature of the materials from which the lens is made.

Soft contact lenses act as efficient substrates for protein deposition and adsorption. This fouling can lead to dehydration of the lens and instability of the tear film, resulting in discomfort and lack of tolerance in the wearer. Adsorption of proteins can also facilitate bacterial colonization and this can increase the risk of vision-threatening infections.

In view of the potential fouling of contact lenses and the problems created by such fouling, as discussed above, it is generally accepted that contact lens cleaning must be a regular part of a patient's lens care regimen. Many different types of cleaning agents have been utilized in the past for this purpose. Cleaning agents such as surfactants and enzymes are typically incorporated into contact lens care products to remove protein deposits. However, the use of these agents can lead to irritation, and in cases where rubbing and cleaning regimens are required, there is a possibility that the cleaning agents will not be used properly or will be used in a manner that damages the lenses. In view of the foregoing problems, it would be advantageous if the surfaces of contact lenses could be modified so as to prevent or reduce the adsorption of proteins to the surfaces.

Various attempts have been made to reduce protein deposit formation on contact lenses. The following patents may be referred to for further background regarding such attempts:

U.S. Pat. No. 4,411,932 describes the use of polymeric alcohols and polymeric ethers, including poly(ethylene glycol), polyethylene oxide and polyethylene glycol methyl ether, as prophylactic agents against soilant deposits on contact lenses;

U.S. Pat. No. 6,274,133 (Hu et al.) describes the use of cationic cellulose polymers to prevent the build-up of lipids and proteins on a silicone-hydrogel lens;

U.S. Pat. No. 6,323,165 (Heiler, et al.) describes the use of charged polyquaternium polymers to block the binding of proteins to hydrophilic contact lenses; and U.S. Pat. No. 6,096,138 (Heiler, et al.) describes the use of polyquaternium polymers such as Luviquat® (BASF), which is a mixture of vinylpyrrolidone and vinylimidazolium moieties that can bind to hydrophilic contact lens materials, so as to block the binding of proteinaceous materials to the lenses.

These prior attempts to reduce protein binding have drawbacks. For example, cationic polymers may act as irritants upon contact with the eye when utilized at high concentrations. Additionally, due to the positive charge character of these macromolecules, complex formation with anionic surfactants or other components of CLC products may lead to flocculation and phase separation in the formulation, which is a significant problem. Accordingly, there is need for new approaches to provide protein resistant surfaces.

Due to the trend toward use of extended wear lenses, it would be useful to be able to provide contact lens wearers with a contact lens surface that inhibits adsorption of proteinaceous matter for extended time periods, without compromising the safety of the patient. The polymer should also be compatible in contact lens care solutions when storage, disinfection and/or cleaning are desired by the patient. The present invention is directed to satisfying these needs.

SUMMARY OF INVENTION

The present invention is directed to the use of polymers that are surface active and exhibit a temperature response in aqueous solutions. The polymers and related polymers (e.g., co-polymers) are formed from a N-isopropylacrylamide ("NIPAM") monomer.

The present invention is based on a discovery that the NIPAM polymers and related polymers may be utilized to inhibit protein deposition on the surfaces of hydrogel contact lenses. The NIPAM polymers provide unique solution properties, and it has been discovered that these properties can be employed in formulations where protein resistant hydrogel surfaces are desired.

As discussed above, there is a need for improved approaches for modifying the adsorption of proteins on the surfaces of contact lenses. The present invention is based on a discovery that the NIPAM polymers described herein are uniquely suited for this purpose.

The NIPAM polymers described herein may be employed in various manners in order to achieve modification of contact lens surfaces and surfaces of other medical devices. For example, contact lenses can be stored in solutions containing NIPAM polymers prior to being worn. This prophylactic approach allows the polymers to form a protective layer on the surface of the lenses before the consumer even exposes the lenses to tear fluids containing protein. The NIPAM polymers may also be incorporated in multi-purpose solutions for treating contact lenses on a daily basis. Chemical grafting on surfaces to form permanent coatings of NIPAM polymers is another method for preparing protein resistant surfaces.

In addition to contact lenses, the surface modification techniques described herein may be applied to various medical devices where protein resistant surfaces are desired, such as intraocular lenses, catheters, cardiac stents, prosthetics, and other medical devices that undergo prolonged exposure to proteins during use in or on the bodies of humans or other mammals.

Although not wishing to be bound by theory it is believed that the NIPAM polymers described herein have a range of inherent physical properties (e.g., low interfacial free energy, hydrophilic-hydrophobic properties, very low toxicity, dynamic surface mobility and steric stabilization) that enable these polymers to exhibit superior protein inhibiting characteristics.

DETAILED DESCRIPTION OF THE INVENTION

Figure 1:
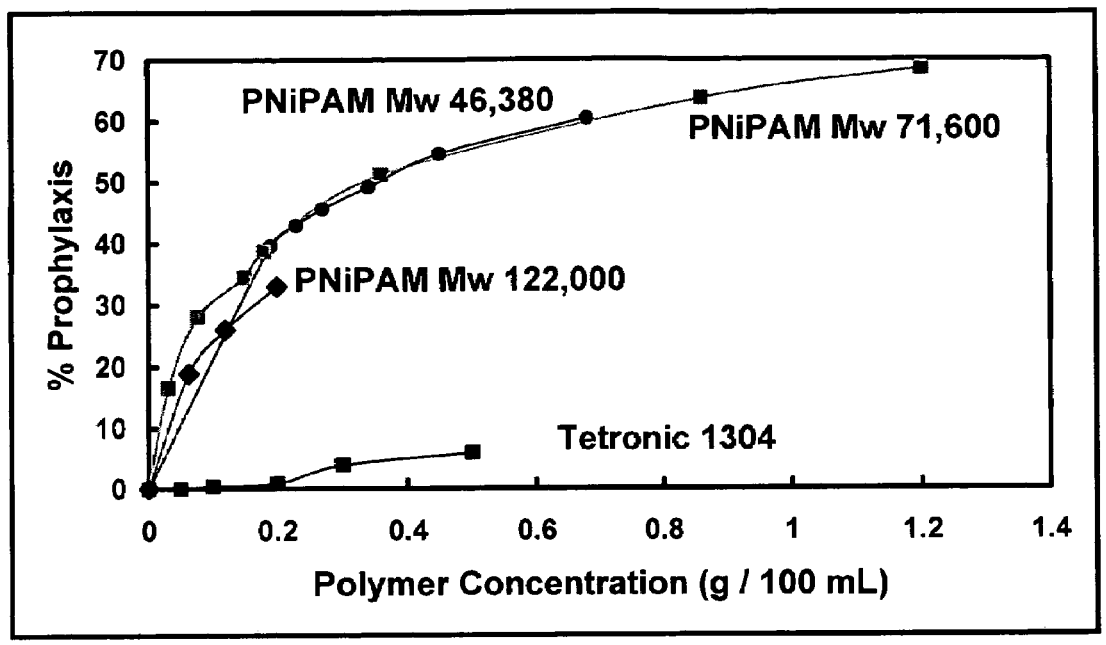
FIG. 1 is a graph showing the results of the tests described in Example 1.

The NIPAM polymers utilized in the present invention have the following formula:

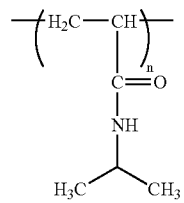

wherein n is a whole number of from 10 to 3,000.

The NIPAM polymers utilized in the present invention include various types of polymers that comprise the above-described monomer. The polymers may be formed entirely from the NIPAM monomer identified above, or other monomers can be incorporated into the polymer by copolymerizing the NIPAM monomer with other monomers, such as acrylic acid, acrylamide, N-acetylacylamide, N,N-dimethylacrylamide and butyl methacrylate. In addition, modified polymers or copolymers containing the NIPAM monomer can be prepared by functionalization of end groups, preparation of block copolymers, and cross-linking of polymers. All such polymers, copolymers or modifications thereof are referred to herein as either "NIPAM polymers" or "PNIPAM". The NIPAM polymers utilized in the present invention will typically have molecular weights of from 1,000 to 300,000 Daltons. The polymers are available from Polymer Source, Inc., Dorval, Quebec (Canada).

The amount of PNIPAM utilized in the compositions of the present invention will vary depending on the form of the compositions and the intended use thereof. The concentration of PNIPAM utilized will generally be an amount sufficient to obtain a solution surface tension of less than 50 milliNewtons per meter ("mNm$^{-1}$") at room temperature (23° C.).

The above-described NIPAM polymers are surface active, and therefore will readily adsorb to most types of surfaces. Factors such as the type of surface (hydrophobic versus hydrophilic), temperature, buffer and excipients will influence the interaction between the polymers and a surface, and will influence the magnitude of the interactions.

The above-described PNIPAM polymers may be combined with other components commonly utilized in products for treating contact lenses, such as rheology modifiers, enzymes, antimicrobial agents, surfactants, chelating agents or combinations thereof. The preferred surfactants include anionic surfactants, such as RLM 100, and nonionic surfactants, such as the poloxamines available under the name "Tetronic®", and the poloxamers available under the name "Pluronic®". Furthermore, a variety of buffering agents may be added, such as sodium borate, boric acid, sodium citrate, citric acid, sodium bicarbonate, phosphate buffers and combinations thereof.

The compositions of the present invention that are intended for use as CLC products will contain one or more ophthalmically acceptable antimicrobial agents in an amount effective to prevent microbial contamination of the compositions (referred to herein as "an amount effective to preserve"), or in an amount effective to disinfect contact lenses by substantially reducing the number of viable microorganisms present on the lenses (referred to herein as "an amount effective to disinfect").

The levels of antimicrobial activity required to preserve ophthalmic compositions from microbial contamination or to disinfect contact lenses are well known to those skilled in the art, based both on personal experience and official, published standards, such as those set forth in the United States Pharmacopoeia ("USP") and similar publications in other countries.

The invention is not limited relative to the types of antimicrobial agents that may be utilized. Examples of antimicrobial agents that may be used include: chlorhexidine, polyhexamethylene biguanide polymers ("PHMB"), polyquaternium-1, and the amino biguanides described in co-pending U.S. patent application Ser. No. 09/581,952, now U.S. Pat. No. 6,664,294, and corresponding International (PCT) Publication No. WO 99/32158, the entire contents of which are hereby incorporated in the present specification by reference.

The preferred antimicrobial agents are polyquaternium-1, and amino biguanides of the type described in U.S. patent application Ser. No. 09/581,952, now U.S. Pat. No. 6,664,294, and corresponding International (PCT) Publication No. WO 99/32158. The most preferred amino biguanide is identified in U.S. patent application Ser. No. 09/581,952, now U.S. Pat. No. 6,664,294, as "Compound Number 1". This compound has the following structure:

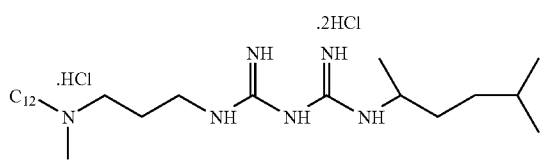

It is referred to below by means of the code number "AL-8496".

The ophthalmic compositions of the present invention will generally be formulated as sterile aqueous solutions. The compositions must be formulated so as to be compatible with ophthalmic tissues and contact lens materials. The compositions will generally have an osmolality of from about 200 to about 400 milliosmoles/kilogram water ("mOsm/kg") and a physiologically compatible pH.

The compositions of the present invention and the ability of those compositions to reduce protein adsorption on contact lenses are further illustrated by the following Examples. Unmodified (i.e., non-ionic) NIPAM polymers and modified (i.e., end terminated with —COOH groups) NIPAM polymers were added to appropriately buffered solutions to demonstrate the ability of these polymers to reduce protein adsorption when utilized as components of buffered multi-purpose solutions for treating contact lenses. A simple means of producing PNIPAM-modified surfaces was used in order to mimic the contact lens disinfection/cleaning regime typically used by the consumer.

EXAMPLE 1

The tests described below were conducted to evaluate the ability of NIPAM polymers to modify contact lens surfaces and thereby reduce protein adsorption.

Materials/Methods

The materials and methods utilized in the evaluation were as follows:

Chemicals

Lysozyme (Sigma, Chicken egg white, grade 1, 3× crystalline), Trifluoroacetic Acid Anhydrous (Sigma, Protein sequencing grade) Acetonitrile (EM Science, HPLC grade), Sodium Phosphate Monobasic, Monohydrate (Sigma, ACS reagent grade), Sodium Phosphate Dibasic, Anhydrous (Sigma, ACS reagent grade), Sodium Chloride (Sigma, ultra pure grade), Unisol®4 (Alcon Laboratories, Inc., preservative-free. pH-balanced saline solution for rinsing)

The NIPAM polymers utilized are identified in Table 1 below. These polymers were purchased from Polymer Source Inc. and were used without further purification.

TABLE 1

| Polymer | Type | $M_v \times 10^3$ | $M_w/M_n$ |
|---|---|---|---|
| P2991-NIPAM | Non-ionic | 46,380 | 2.36 |
| P604-NIPAM | Non-ionic | 71,600 | 2.44 |
| P1239-NIPAM | Non-ionic | 122,000 | 2.50 |
| P2426F2-NIPAM-COOH | Anionic | 132,000 | 1.29 |

Lenses

Acuvue (Vistakon, a division of Johnson & Johnson Vision Products, Inc) lenses were used as the substrate in this study. The lenses had the following parameters: 42% etafilcon A, 58% water, FDA Group IV lens. Diameter, 14.0 mm; base curve, 8.8 mm; power, −2.00.

Formulations

The NIPAM and NIPAM-COOH polymers identified in Table 1 were formulated at pH 7.8 in a buffered vehicle containing 1.5% sorbitol, 0.6% boric acid and 0.32% NaCl. In a beaker, all the formulation chemicals except for the NIPAM polymers were weighed out and purified water was added (QS to 95%). The pH was adjusted to 7.8 with NaOH/HCl. The NIPAM polymer was weighed out and added to the buffer solution and this was stirred overnight to solubilize the polymer. The test formulations are shown in Table 2 below; the concentrations are expressed as weight/volume percent ("w/v %"):

TABLE 2

| | Formulation Numbers | | |
|---|---|---|---|
| Component | 9591-47A | 9591-47B | 9591-47C (Control) |
| P2991-NIPAM | 0.034 | 0.017 | — |
| Sorbitol | 1.5 | 1.5 | 1.5 |
| Boric Acid | 0.6 | 0.6 | 0.6 |
| Sodium Chloride | 0.32 | 0.32 | 0.32 |
| Purified Water | QS | QS | QS |
| pH | 7.8 | 7.8 | 7.8 |

The test formulations were evaluated for their prophylaxis behavior using lysozyme as the model protein, as described below.

Preparation of Deposition Solution

Phosphate Buffered Saline (PBS) 1.311 g of monobasic sodium phosphate (monohydrate), 5.74 g of dibasic sodium phosphate (anhydrous), and 9.0 g of sodium chloride were dissolved in deionized water and the volume was brought to 1000 mL with deionized water, and pH was adjusted (as necessary). The final concentrations of sodium phosphate and sodium chloride were 0.05 M and 0.9%, respectively. The final pH was 7.4.

Lysozyme Solution

A 1.5-mg/mL lysozyme solution was prepared by dissolving 750 mg of lysozyme in 500-mL phosphate buffered saline pH adjusted to 7.4.

Lens Extraction Solution (ACN/TFA)

A lens extraction solution was prepared by mixing 1.0 ml of trifluoroacetic acid with 500-mL acetonitrile and 500 ml of deionized water. The pH of the solution ranged from 1.5 to 2.0.

Lens Presoak Procedure

Each lens was immersed in 3-mL of each test formulation and allowed to sit at room temperature overnight. The next morning, the lenses were removed from the test formulations and dabbed lightly on a towel.

Lens Deposition Procedure (Physiological Deposition Model)

Each presoaked lens was immersed in a Wheaton glass sample vial containing 3-mL of lysozyme solution. The vial was closed with a plastic snap cap and incubated in a constant temperature water bath at 37° C. for 24 hours. Three additional lenses were included as controls to establish the total amount of lysozyme deposited. After incubation, the deposited lenses were removed from their vials and rinsed by dipping into three consecutive beakers containing 200 ml Unisol®4 or water to remove any excess of the deposition solution.

Extraction and Determination of Lysozyme Extraction

The lenses were extracted with 5 ml of ACN/TFA extraction solution in a screw-capped glass scintillation vial. The extraction was done by shaking the vial with a rotary shaker (Red Rotor) at room temperature for at least 2 hours (usually overnight).

Calculations for the Determination of Lysozyme

Quantitative determination of the lysozyme of the lens extract was carried out using a fluorescence spectrophotometer interfaced with an autosampler and a computer. The fluorescence intensity of a 2 ml aliquot from each sample solution was measured by setting the excitation/emission wavelength at 280 nm/346 nm with excitation/emission slits of 2.5 nm/10 nm, respectively, and the sensitivity of the photomultiplier was set at 950 volts.

A lysozyme standard curve was established by diluting the lysozyme stock solution to concentrations ranging from 0 to 40 µg/ml, using the ACN/TFA extraction solution for the lens extract and the vehicle for the soaking solutions. The instrument settings for measuring the fluorescence intensity were the same for the lens extracts and lens soaking solutions.

The lysozyme concentrations for all of the samples were calculated based on the slope developed from the linear lysozyme standard curve. The % prophylaxis of each formulation was calculated by subtracting the amount of lysozyme in the lens extract from the amount of lysozyme from the control lenses (total deposit), then dividing that by the total deposit and multiplying by 100.

Results

FIG. 1 shows the % prophylaxis as a function of PNIPAM concentration (g/100 ml) for nonionic NIPAM polymers having molecular weights of 46,380; 71,600; and 122,000, respectively.

FIG. 1 shows that there was no significant PNIPAM molecular weight dependence on the % prophylaxis using the defined polymer concentrations. PNIPAM concentrations up to 0.2 g/100 ml gave % prophylaxis results of approximately 30%. With increasing PNIPAM concentrations above 0.2 g /100 ml the % prophylaxis could be increased to 50% to 60% using polymer concentrations between 0.4 g/100 ml and 0.65 g /100 ml. The % prophylaxis was not dependent on the molecular weight of the NIPAM polymers.

EXAMPLE 2

The prophylactic properties of NIPAM polymers were further evaluated using a 3-day cycling study. Two sets of lenses were prepared. One set was presoaked in the formulations shown in Table 2 before going into the lysozyme solution, whereas the other set was not. Both sets of lenses were then placed in the lysozyme solution for 8 hours (Day 1). At the end of the day all the lenses were rinsed and put in their respective formulations to soak overnight. The following day (Day 2), the lenses went back into the lysozyme for the day (8 hours). This was repeated to complete 3 cycles (3 Days). At the end of the experiment all the lenses were analyzed in accordance with the procedures described in Example 1. The results are presented in Table 3:

TABLE 3

| Sample | Uptake of Lysozyme (ug/lens) | sd | Amount Removed (ug/lens) | % Prophylaxis | sd |
|---|---|---|---|---|---|
| 9591-47A(PS) | 124.1 | 9.1 | 261.9 | 67.8 | 0.8 |
| 9591-47B(PS) | 151.5 | 3.9 | 234.5 | 60.8 | 0.6 |
| 9591-47C(PS) | 386.0 | 6.1 | — | — | — |
| 9591-47A | 206.3 | 2.7 | 174.9 | 45.9 | 1.2 |
| 9591-47B | 221.3 | 10.4 | 159.9 | 41.9 | 0.9 |
| 9591-47C | 381.2 | 7.1 | — | — | — |

PS = Presoaked

The results demonstrate that the buffered solutions containing a NIPAM polymer (i.e., P2991-NIPAM) were effective in reducing protein uptake in both the presoaked and non-presoaked lenses. For example, the presoaked lenses treated with solutions containing concentrations of 0.034% and 0.017% of the NIPAM polymer demonstrated prophylaxis values of 67.8% and 60.8%, respectively. For the non-presoaked lenses the prophylaxis values were 45.9% and 41.9% at concentrations of 0.034% and 0.017%, respectively.

The results set forth in Table 3 demonstrate that treatment of the lenses with a NIPAM polymer solution prior to exposure to proteins is preferable. However, the results also show that even when the lenses have already been exposed to proteins prior to an initial treatment with a NIPAM polymer solution, the uptake of protein is reduced when the lenses are subsequently treated with a NIPAM polymer solution. Thus, the results of this study confirm that the compositions of the present invention are effective in reducing the formation of protein deposits on contact lenses, even when the lenses are repeatedly exposed to protein contamination.

EXAMPLE 3

The prophylaxis work was extended to formulations containing the antimicrobial agent AL-8496 with unmodified NIPAM (non-ionic) and modified NIPAM (end functionalized with COOH) polymers. The formulations evaluated are shown in Table 4, below:

TABLE 4

Formulations for Microbiology Evaluation of PNIPAM Formulations Containing A Contact Lens Disinfecting Agent (AL-8496)

| Component | Formulation Numbers | | | | | |
|---|---|---|---|---|---|---|
| | 9591-44B | 9591-44C | 9591-44D | 9591-44E | 9591-44F | 9591-44I (Control) |
| P2991-NIPAM | 0.087 | 0.21 | | | | |
| P2426F2-NIPAMCOOH | | | 0.040 | 0.10 | 0.25 | |
| AL-8496* | 0.0004 | 0.0004 | 0.0004 | 0.0004 | 0.0004 | 0.0004 |
| Tetronic ® 1304 | 0.1 | 0.1 | 0.1 | 0.1 | 0.1 | 0.1 |
| Sorbitol | 0.4 | 0.4 | 0.4 | 0.4 | 0.4 | 0.4 |
| Sodium borate | 0.2 | 0.2 | 0.2 | 0.2 | 0.2 | 0.2 |
| Sodium citrate | 0.6 | 0.6 | 0.6 | 0.6 | 0.6 | 0.6 |
| Propylene glycol | 1.0 | 1.0 | 1.0 | 1.0 | 1.0 | 1.0 |
| Disodium edetate | 0.05 | 0.05 | 0.05 | 0.05 | 0.05 | 0.05 |
| pH | 7.8 | 7.8 | 7.8 | 7.8 | 7.8 | 7.8 |
| % Prophylaxis | 37.4 ± 0.2 | 54.1 ± 1.0 | 51.0 ± 0.5 | 57.3 ± 0.4 | 62.8 ± 1.2 | 0.6 ± 0.0 |

*As base

Figure 2:
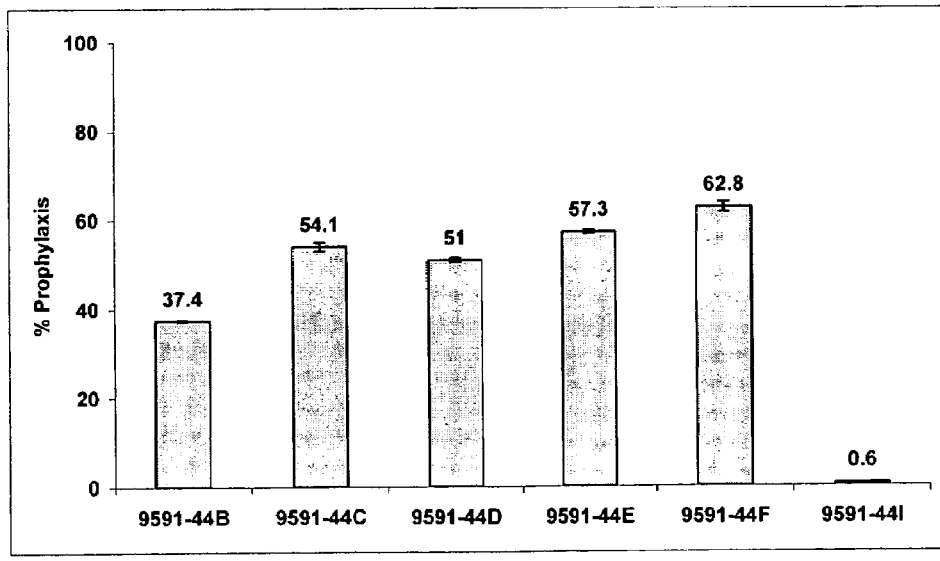
FIG. 2 is a graph showing the results of the tests described in Example 3.

The procedures utilized were the same as in Example 1. FIG. 2 shows the prophylaxis data obtained using the overnight soak model with lenses pre-soaked in the respective PNIPAM formulations.

FIG. 2 shows that the prophylaxis properties of the NIPAM polymers were retained in the presence of the antimicrobial agent AL-8496 and other formulation components, including cleaning ingredients (e.g., citrate and Tetronic® 1304). The data demonstrate that both unmodified and modified NIPAM polymers can be incorporated into multi-purpose contact lens care formulations without compromising the prophylactic properties of the polymers.

EXAMPLE 4

The disinfection activity of the formulations shown in Table 4 above was also evaluated. The results are shown in Table 5 below.

TABLE 5

Disinfection Properties of PNIPAM Formulations containing AL-8496

| Microorganism | Time (hrs) | 9591-44B | 9591-44C | 9591-44D | 9591-44E | 9591-44F | 9591-44I |
|---|---|---|---|---|---|---|---|
| Candida albicans | 6 | 2.8 | 3.0 | 3.0 | 3.4 | 3.2 | 3.0 |
| | 24 | 3.9 | 4.5 | 6.0 | 6.0 | 5.3 | 6.0 |
| Serratia marcescens | 6 | 2.7 | 6.2 | 2.8 | 2.7 | 2.6 | 2.6 |
| | 24 | 5.5 | 6.2 | 5.5 | 6.2 | 5.5 | 4.9 |
| Staphylococcus aureus | 6 | 5.5 | 4.5 | 5.5 | 4.4 | 4.3 | 4.9 |
| | 24 | 6.2 | 5.0 | 6.2 | 6.2 | 6.2 | 5.2 |

The results demonstrate that the NIPAM polymers did not adversely affect the antimicrobial activity of the antimicrobial agent AL-8496.

EXAMPLE 5

Several formulations were evaluated to compare the prophylaxis properties of PNIPAM with two well-known block co-polymers, Tetronic® 1107 and Pluronic® F127. The formulation components and prophylaxis results are given in Table 6, below.

The evaluation was carried out using the same procedures as outlined in Example 1. The buffered solution utilized as a control (10581-85J) did not exhibit any prophylaxis properties. However, as shown in Table 6, the compositions of the present invention containing PNIPAM at concentrations of 0.2% (10581-85B) and 0.4% (10581-85C) produced prophylaxis results of 56.2% and 63%, respectively.

In contrast, the solutions containing Tetronic® 1107 and Pluronic® F127 block co-polymers at concentrations of up to 0.8% did not produce any significant prophylaxis.

TABLE 6

| Components | 10581-85B | 10581-85C | 10581-85E | 10581-85F | 10581-85H | 10581-85I | 10581-85J |
|---|---|---|---|---|---|---|---|
| PNIPAM P2991 | 0.2 | 0.4 | — | — | — | — | — |
| Tetronic ® 1107 | — | — | 0.4 | 0.8 | — | — | — |
| Pluronic ® F127 | — | — | — | — | 0.4 | 0.8 | — |
| Sorbitol | 1.5 | 1.5 | 1.5 | 1.5 | 1.5 | 1.5 | 1.5 |
| Boric Acid | 0.6 | 0.6 | 0.6 | 0.6 | 0.6 | 0.6 | 0.6 |
| Sodium Chloride | 0.32 | 0.32 | 0.32 | 0.32 | 0.32 | 0.32 | 0.32 |
| Purified Water | QS | QS | QS | QS | QS | QS | QS |
| pH | 7.8 | 7.8 | 7.8 | 7.8 | 7.8 | 7.8 | 7.8 |
| % Prophylaxis | 56.2 + 0.1 | 63.0 + 0.4 | 0.00 + 2.3 | 4.1 + 2.2 | 0.0 + 2.1 | 0.0 + 0.9 | 0.8 + 1.0 |

I claim:

1. A sterile, aqueous solution for treating contact lenses, comprising: (a) an amount of a NIPAM polymer effective to inhibit the formation of protein deposits on said lenses and sufficient to provide said solution with a surface tension of less than 50 mnM$^{-1}$ at a temperature of 23° C.; (b) an ophthalmically acceptable vehicle for said NIPAM polymer; and (c) an opthalmically acceptable antimicrobial agent in an amount effective to disinfect contact lenses, said solution having a physiologically compatible pH and an osmolality of 200 to 400 mOsm/kg, characterized in that, when said solution is applied to the surfaces of a contact lens, the adsorption of lysozyme to said surfaces following such application is inhibited.

2. The solution of claim 1 wherein the solution contains the NIPAM polymer in an amount sufficient to provide the solution with a surface tension of less than 50 mNm$_{-1}$ at a temperature of 23° C.

3. The solution of claim 1 wherein the solution is a multi-purpose solution suitable for treating contact lenses on a daily basis, and further comprises an effective amount of a surfactant.

* * * * *